(12) United States Patent
Middleton

(10) Patent No.: US 6,654,971 B1
(45) Date of Patent: Dec. 2, 2003

(54) AIR FRESHENING DEVICE FOR TOILETS

(76) Inventor: Eric Middleton, 498 New Jersey Ave., Brooklyn, NY (US) 11207

( * ) Notice: Subject to any disclaimer, the term of this patent is extended or adjusted under 35 U.S.C. 154(b) by 0 days.

(21) Appl. No.: 10/314,976

(22) Filed: Dec. 10, 2002

(51) Int. Cl.⁷ .................................................. E03D 9/00
(52) U.S. Cl. ...................................................... 4/228.1
(58) Field of Search .................. 4/228.1, 229, 231, 4/223

(56) References Cited

U.S. PATENT DOCUMENTS

| | | | | | |
|---|---|---|---|---|---|
| 2,795,799 A | * | 6/1957 | Dickerman | ................ | 4/222 |
| 3,088,125 A | * | 5/1963 | Southwood | ................ | 4/222 |
| 3,316,559 A | * | 5/1967 | Ewing et al. | ................ | 4/223 |
| 3,344,441 A | * | 10/1967 | Kelly | ................ | 4/233 |
| 3,605,133 A | * | 9/1971 | Quercia et al. | ................ | 4/231 |
| 4,670,916 A | * | 6/1987 | Bloom | ................ | 4/231 |

* cited by examiner

Primary Examiner—Gregory L. Huson
Assistant Examiner—Huyen Le
(74) Attorney, Agent, or Firm—I. Zborovsky

(57) ABSTRACT

An air freshening device a toilet, comprising a source of air freshening medium; and an actuating element operatable by a seat of a toilet so that when a user stands up from the seat said actuating element causes discharge of the air freshening medium from said source.

11 Claims, 2 Drawing Sheets

AIR FRESHENING DEVICE FOR TOILETS

BACKGROUND OF THE INVENTION

The present invention relates to an air freshening device for toilets.

Air freshening devices are generally known in the art. Air freshening devices, including those which are used in toilets, conventionally are sources of air freshening medium and are activated by a user for example manually, to produce an air freshening medium spray. The existing devices can be further improved.

SUMMARY OF THE INVENTION

Accordingly, it is an object of the present invention to provide an air freshening device for toilets, which is a further improvement of the existing devices.

In keeping with these objects and with others which will become apparent hereinafter, one feature of the present invention resides, briefly stated, in an air freshening device for a toilet which has a source of air freshening medium; and an actuating element operatable by a seat of a toilet so that when a user stands up from the seat said actuating element causes discharge of the air freshening medium from said source.

When the air freshening device is designed in accordance with the present invention, then automatically when a user after using the toilet stands up, the air freshening device causes discharge of an air freshening medium.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
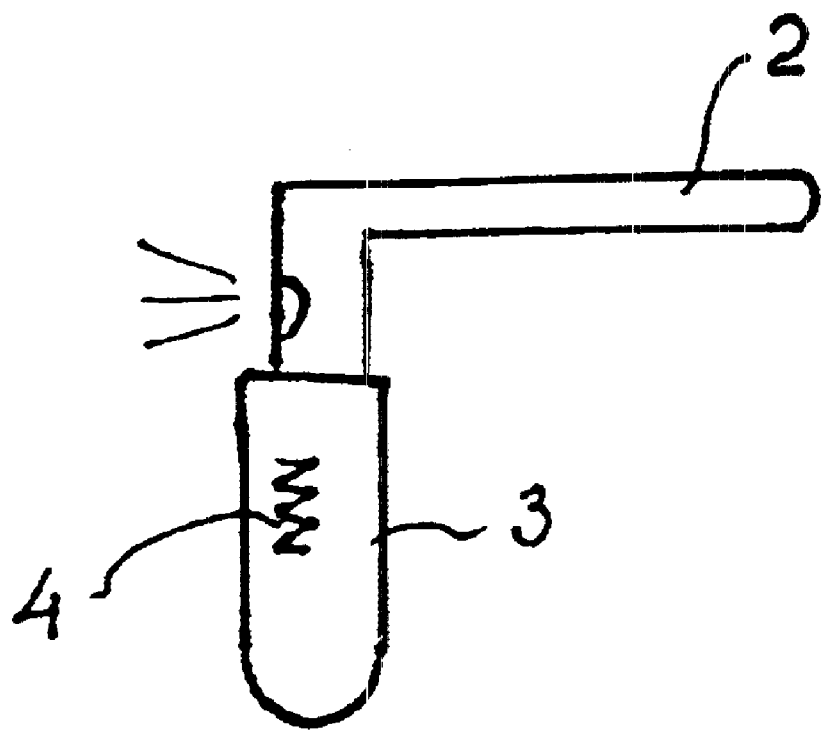
FIG. 1 is a view showing an air freshening medium discharge unit of a device for air freshening according to the present invention.
Figure 2:
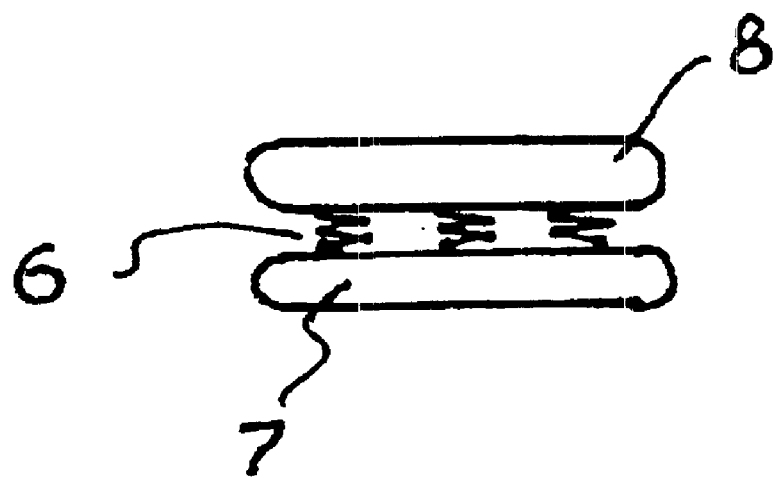
FIG. 2 is a view showing a spring unit of the device according to the present invention.
Figure 3:
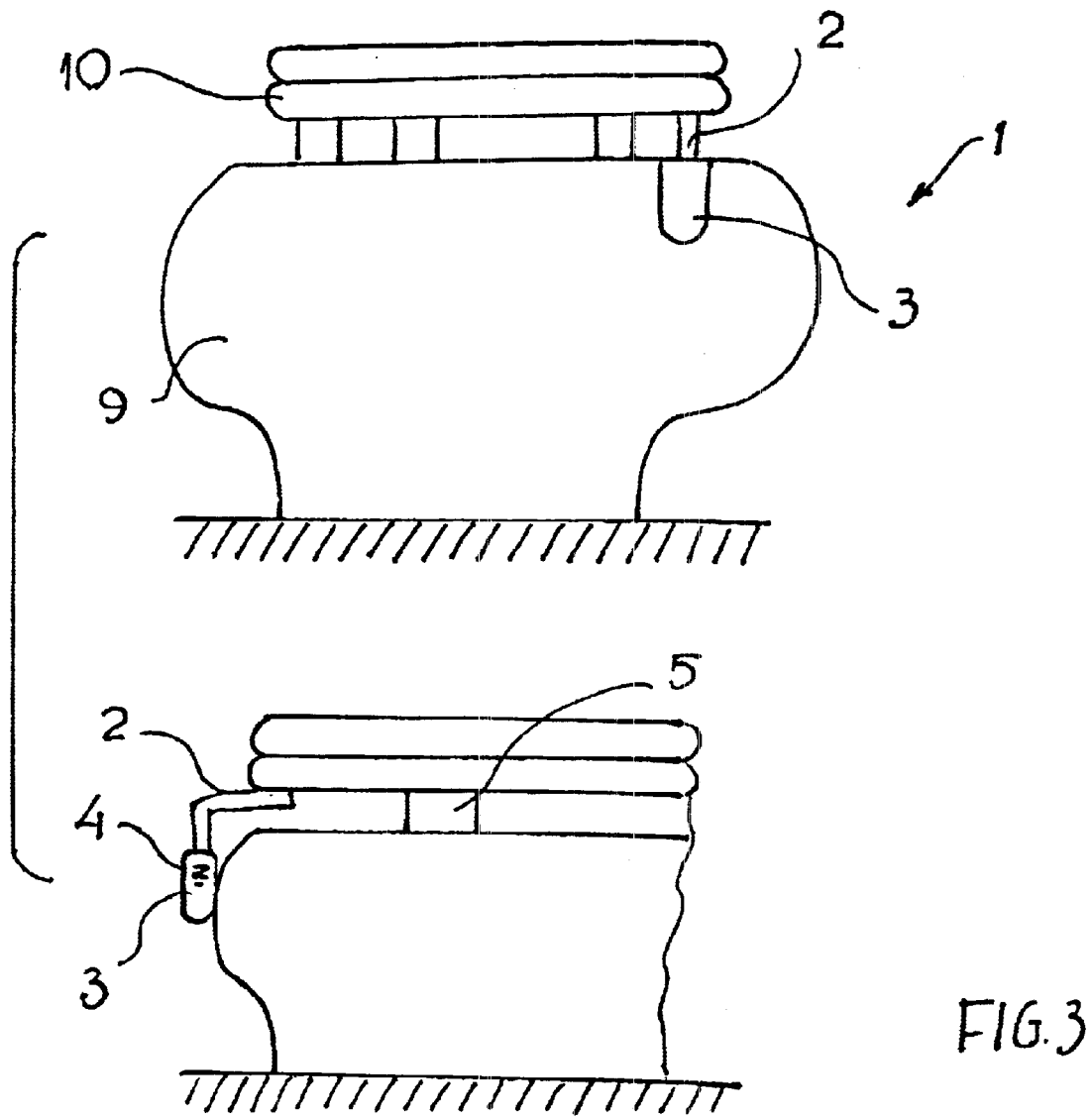
FIG. 3 is a view showing a toilet bowl with a toilet seat and an air freshening device in accordance with the present invention.

FIG. 1 is a view showing an air freshening unit of a device for air freshening in toilets in accordance with the present invention. The air freshening unit is identified in whole as reference numeral 1. The air freshening unit 1 has a handle which is identified as reference numeral 2 and is depressable downwardly and liftable. A source of air freshening medium, for example a container, is identified in reference numeral 3. The interior design of the source is not shown, but it can be provided with a medium discharge unit formed as in well known atomizers for atomization of air freshening substances, perfumes, etc. The only difference is that the medium discharging unit is formed in an opposite way, in particular when the lever 2 is pressed down it does not activate a discharge, but when the lever 2 is moved upwardly it does activate the discharge. The lever 2 can be moved upwardly by a spring which shown only schematically and identified with reference numeral 4.

The device in accordance with the present invention further has a spring unit identified as a whole with reference numeral 5. It can be composed of springs 6 which are located between a rubber base 7 and a plastic cover 8. The spring unit 5 is placed between the upper surface of a toilet bowl 9 and a seat 10. The lever 2 of the air freshening unit is also placed in the same area under the seat 10. The air freshening medium source 3 can be attached for example to the side of the toilet bowl. Alternatingly, the air freshening medium source 3 can be attached to the toilet bowl, for example by a bracket which is insertable into the interior of the toilet bowl, as well known for sanitation packages for the toilet bowls.

The device for air freshening in accordance with the present invention operates in the following manner.

When a user sits on the toilet seat, it depresses the spring unit and pushes the lever of the air freshening unit down. After the user has used the toilet and stands up, the spring unit biases the-seat upwardly and the seat lightly smoves upwardly so that the lever of the air freshening unit is urged by a spring upwardly as well. As a result of the upward movement of the lever, the air freshening medium is discharged from a discharge opening of the air freshening unit.

Therefore it is clear that the device automatically provides discharging of an air freshening medium in places where a toilet bowl installed, as a result of simple user's leaving the toilet seat after he or she has used the toilet.

It will be understood that each of the elements described above, or two or more together, may also find a useful application in other types of constructions and methods differing from the types described above.

While the invention has been illustrated and described as embodied in an air freshening device for toilets, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is:

1. An air freshening device for a toilet, comprising a source of an air freshening medium and an actuating element operatable by a seat of a toilet so that when a user stands up fro the seat said actuating element causes discharge of the air freshening medium from said source, said source of an air freshening medium being, formed as a container, said actuating element being formed as a lever with one portion extending in an interior of said container and another portion extending outside of said container, and spring means urging said lever upwardly; and a spring unit to be placed between an upper surface of a toilet bowl and a seat, so that when a user sits on the seat said spring unit is compressed, and when a user stands up from the seat said spring unit urges the seat upwardly and said lever is moved by said spring means upwardly and causes the discharge of the air freshening medium from said container.

2. An air freshening device as defined in claim 1, wherein said one portion of said lever is substantially vertical, while the other portion of said lever is substantially horizontal and adapted to be placed under the seat of the toilet.

3. An air freshening device as defined in claim 2, wherein said substantially vertical portion of said lever is provided with an outlet opening for discharging the air freshening medium.

4. An air freshening device as defined in claim 1, wherein said spring unit includes an upper member, a lower member and a plurality of springs located between said members.

5. An air freshening device as defined in claim 4, wherein said upper member is formed as a plastic cover and said lower member is formed as a rubber base.

6. A toilet unit: comprising a toilet bowl; a toilet seat movable between a lifted and a lowered position; and a device for freshening air, said air freshening device including a source of an air freshening medium, and an actuating element operatable by said seat of a toilet so that when a user stands up from the seat said actuating element causes discharge of the air freshening medium from said source, said source of an air freshening medium being, formed as a container, said actuating element being formed as a lever with one portion extending in an interior of said container and another portion extending outside of said container; and spring means urging said lever upwardly, and a spring unit to be placed between an upper surface of a toilet bowl and a seat, so that when a user sits on the seat said spring unit is compressed, and when a user stands up from the seat said spring unit urges the seat upwardly and said lever is moved by said spring means upwardly and causes the discharge of the air freshening medium from said container.

7. A toilet unit as defined in claim 6, wherein said one portion of said lever is substantially vertical, while the other portion of said lever is substantially horizontal and adapted to be placed under the seat of the toilet.

8. A toilet unit as defined in claim 6, wherein said substantially vertical portion of said lever is provided with an outlet opening for discharging the air freshening medium.

9. A toilet unit as defined in claim 6, wherein said spring unit includes an upper member, a lower member and a plurality of springs located between said members.

10. A toilet unit defined in claim 9, wherein said upper member is formed as a plastic cover and said lower member is formed as a rubber base.

11. An air freshening device for a toilet, comprising a source of an air freshening medium, and an actuating element operatable by a seat of a toilet so that when a user stands up fro the seat said actuating element causes discharge of the air freshening medium from said source, said source of an air freshening medium being, formed as a container, said actuating element being formed as a lever with one portion extending in an interior of said container and another portion extending outside of said container, and spring means urging said lever upwardly, and a spring unit to be placed between an upper surface of a toilet bowl and a seat, so that when a user sits on the seat said spring unit is compressed, and when a user stands up from the seat said spring unit urges the seat upwardly and said lever is moved by said spring means upwardly and causes the discharge of the air freshening medium from said container, said one portion of said lever being substantially vertical and provided with an outlet opening for discharging the air freshening medium, said other portion of said lever being substantially horizontal and adapted to be placed between the upper surface of a toilet bowl and the seat, and said spring unit having an upper member and a lower member and plurality of springs located between said upper member and said lower member.

\* \* \* \* \*